US012330323B2

(12) United States Patent
Tellez et al.

(10) Patent No.: US 12,330,323 B2
(45) Date of Patent: Jun. 17, 2025

(54) SUCTION ATTACHMENTS FOR SURGICAL HAIR CLIPPERS AND METHODS OF USING SUCH SUCTION ATTACHMENTS

(71) Applicant: CareFusion 2200,Inc., San Diego, CA (US)

(72) Inventors: Isaias Tellez, Kenosha, WI (US); Robert Radford, Skokie, IL (US); Camille A. Sendlak, Arlington Heights, IL (US); Sara Tillman, Vernon Hills, IL (US)

(73) Assignee: CareFusion 2200, Inc., San Diego, CA (US)

( * ) Notice: Subject to any disclaimer, the term of this patent is extended or adjusted under 35 U.S.C. 154(b) by 509 days.

(21) Appl. No.: 17/072,515

(22) Filed: Oct. 16, 2020

(65) Prior Publication Data

US 2021/0114242 A1    Apr. 22, 2021

Related U.S. Application Data

(60) Provisional application No. 62/916,551, filed on Oct. 17, 2019.

(51) Int. Cl.
| | |
|---|---|
| *B26B 19/44* | (2006.01) |
| *A61B 17/00* | (2006.01) |
| *B26B 19/02* | (2006.01) |
| *B26B 19/38* | (2006.01) |
| *B26B 19/42* | (2006.01) |

(52) U.S. Cl.
CPC ........ *B26B 19/44* (2013.01); *A61B 17/00234* (2013.01); *B26B 19/02* (2013.01); *B26B 19/3813* (2013.01); *B26B 19/3846* (2013.01); *B26B 19/3853* (2013.01); *B26B 19/42* (2013.01)

(58) Field of Classification Search
CPC ..... B26B 19/00; B26B 19/44; B26B 19/3806; B26B 19/3813; B26B 19/3853; B26B 19/386
See application file for complete search history.

(56) References Cited

U.S. PATENT DOCUMENTS

| | | | | |
|---|---|---|---|---|
| 2,748,472 A | * | 6/1956 | Sheley | B26B 19/44 30/41.5 |
| 3,073,026 A | * | 1/1963 | Schaedler | B26B 19/44 30/133 |
| 3,280,456 A | * | 10/1966 | Erickson | B26B 19/205 30/201 |

(Continued)

FOREIGN PATENT DOCUMENTS

EP    1775079 A1 *  4/2007    ............. B26B 19/06

*Primary Examiner* — Adam J Eiseman
*Assistant Examiner* — Richard D Crosby, Jr.
(74) *Attorney, Agent, or Firm* — Dinsmore & Shohl LLP (57) ABSTRACT

A surgical hair clipper assembly includes a clipper body and a blade assembly connected to the clipper body. The blade assembly includes a moveable blade configured to reciprocate to remove hair from a skin area and a blade housing that houses the moveable blade. The blade housing has a guide surface that faces the skin area during a hair removal process. A suction attachment includes a clipper attachment connected to the clipper body and a nozzle structure connected to the clipper attachment and extending distally to an end. The end is located no more than about ten millimeters proximal of a plane defined by the guide surface.

14 Claims, 6 Drawing Sheets

(56) References Cited

U.S. PATENT DOCUMENTS

| | | | | |
|---|---|---|---|---|
| 3,331,130 A * | 7/1967 | Ligon | B26B 19/44 | 30/133 |
| 3,348,308 A * | 10/1967 | Andis | B26B 19/44 | 30/133 |
| 3,368,277 A * | 2/1968 | Vevea | B26B 19/34 | 30/41.5 |
| 3,384,919 A * | 5/1968 | Jording | B26B 19/44 | 30/133 |
| 4,077,122 A * | 3/1978 | Rollor, Jr. | B26B 19/44 | 30/41.5 |
| 4,216,581 A * | 8/1980 | Van Slooten | B26B 19/42 | 30/133 |
| 4,628,601 A * | 12/1986 | Van Slooten | B26B 19/44 | 30/201 |
| 4,843,717 A * | 7/1989 | Crane | B26B 19/44 | 30/41.6 |
| 4,972,584 A * | 11/1990 | Baumann | B26B 19/44 | 30/201 |
| 5,088,199 A * | 2/1992 | Romani | B26B 19/44 | 30/132 |
| 5,142,786 A * | 9/1992 | Hunts | B26B 19/44 | 30/201 |
| D348,543 S * | 7/1994 | Melton | D28/54 | |
| 5,377,411 A * | 1/1995 | Andriotis | B26B 19/44 | 30/253 |
| 5,924,202 A * | 7/1999 | Romani | B26B 19/44 | 30/132 |
| 6,442,842 B1 * | 9/2002 | Parry | B26B 19/44 | 30/201 |
| 6,571,478 B1 * | 6/2003 | Romani | B26B 19/44 | 30/132 |
| 7,488,004 B1 * | 2/2009 | Romani | A47L 7/009 | 285/280 |
| 8,225,512 B2 * | 7/2012 | Coleman | B26B 19/3813 | 30/41.6 |
| 8,484,853 B1 * | 7/2013 | Laube | B26B 19/44 | 30/216 |
| 8,555,463 B1 * | 10/2013 | Laube | A47L 7/009 | 119/606 |
| 8,561,303 B2 * | 10/2013 | Landrie | A45D 44/00 | 30/41.6 |
| 2002/0073550 A1 * | 6/2002 | Long | B26B 19/44 | 30/41.6 |
| 2002/0108255 A1 * | 8/2002 | Degregorio, Jr. | B26B 19/44 | 30/208 |
| 2004/0006873 A1 * | 1/2004 | Cutting | B26B 19/20 | 30/133 |
| 2004/0045168 A1 * | 3/2004 | Talavera | B26B 19/3813 | 30/30 |
| 2006/0162516 A1 * | 7/2006 | Andis | B26B 19/3853 | 83/13 |
| 2008/0250649 A1 * | 10/2008 | Spigai | B26B 19/40 | 30/133 |
| 2009/0223058 A1 * | 9/2009 | Coleman | B26B 19/3813 | 30/41.6 |
| 2011/0185578 A1 * | 8/2011 | Landrie | A45D 44/00 | 132/200 |
| 2012/0318300 A1 * | 12/2012 | Panzer | B26B 19/44 | 55/495 |
| 2013/0269191 A1 * | 10/2013 | Landrie | B26B 19/44 | 30/133 |
| 2015/0246454 A1 * | 9/2015 | Mintz | B26B 19/44 | 30/124 |
| 2016/0361826 A1 * | 12/2016 | Musallam | B26B 19/06 | |
| 2017/0361479 A1 * | 12/2017 | Magrone | B26B 19/3886 | |
| 2018/0222068 A1 * | 8/2018 | Halmut | B26B 19/20 | |
| 2020/0078953 A1 * | 3/2020 | Dai | B26B 19/388 | |
| 2020/0298431 A1 * | 9/2020 | Huang | B26B 19/06 | |

* cited by examiner

SUCTION ATTACHMENTS FOR SURGICAL HAIR CLIPPERS AND METHODS OF USING SUCH SUCTION ATTACHMENTS

CROSS-REFERENCE

The present application claims the benefit of and priority to U.S. Provisional Patent Application No. 62/916,551, filed Oct. 17, 2019 titled "Suction Attachments for Surgical Hair Clippers and Methods of Using Such Suction Attachments," the details of which are incorporated by reference in their entirety.

TECHNICAL FIELD

The present disclosure generally relates to surgical hair clippers and methods of use, and more specifically, to suction attachments for surgical hair clippers and methods of their use.

BACKGROUND

Surgical clippers include blade assemblies that assist with hair removal from the body of a patient in preparation for surgery or other medical procedures for which a skin area of the patient needs to be cleared of hair. Use of surgical clippers by healthcare personnel for hair removal from the skin area may reduce a risk of cuts and abrasions compared to, for example, use of razor blades. It is common to remove hair clippings once they have been cut. One common method of removing hair clippings includes use of an adhesive tape that is pressed against the hair clippings and the skin and then lifted with the hair clippings adhered to the adhesive side of the tape. This method using tape can be inefficient and leave hair behind. In addition, the patient may have an allergic reaction to the adhesive used on the tape.

Vacuum devices have been introduced where a vacuum nozzle is used to pick up hair clippings. Some of these vacuum devices attach to surgical hair clippers to remove hair clippings as they are being cut. Some of these vacuum devices may allow for improper uses of the surgical clippers, such as raking of the blades against the skin, because nozzles of the vacuum devices are removed from the blades thereby exposing the blades to a variety of cutting angles many of which may not be optimum.

Accordingly, a need exists for suction attachments for surgical hair clippers that reinforce proper technique while improving hair removal and clipping.

SUMMARY

According to one embodiment, a surgical hair clipper assembly includes a clipper body and a blade assembly connected to the clipper body. The blade assembly includes a moveable blade configured to reciprocate to remove hair from a skin area and a blade housing that houses the moveable blade. The blade housing has a guide surface that faces the skin area during a hair removal process. A suction attachment includes a clipper attachment connected to the clipper body and a nozzle structure connected to the clipper attachment and extending distally to an end. The end is located no more than about ten millimeters proximal of a plane defined by the guide surface.

According to another embodiment, a suction attachment includes a clipper attachment that connects to a clipper body of a surgical hair clipper. A nozzle structure is connected to the clipper attachment. The nozzle structure has a hose connecting end and a suction end. A length of a leading side of the nozzle structure is greater than a length of a trailing side of the nozzle structure such that the suction end contacts a skin area during use.

According to another embodiment, a method of using a surgical hair clipper with a suction attachment is provided. The method includes attaching a clipper attachment about a clipper body of the surgical hair clipper such that a nozzle structure of the suction attachment is located adjacent a blade assembly of the surgical hair clipper. The blade assembly includes a blade housing having a guide surface that faces the skin area during a hair removal process. The suction attachment includes the clipper attachment connected to the clipper body and the nozzle structure connected to the clipper attachment and extending distally to an end. The end is located no more than about ten millimeters proximal of a plane defined by the guide surface. Hair is cut while contacting a skin area of a patient with the end of the nozzle structure.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

A suction attachment for a surgical hair clipper is described herein that includes a clipper attachment and a nozzle structure that is connected to the clipper attachment. The clipper attachment includes an attachment body that is used to secure the suction attachment to the surgical hair clipper, around a blade assembly. The nozzle structure is located in front of the blade assembly when the clipper attachment is connected to the surgical hair clipper so that hair clippings are collected as they are being cut. In some embodiments, the nozzle structure may have a length such that the nozzle structure contacts a skin area in front of the blade assembly during a hair removal process. The nozzle structure may include, for example, a roller or other skin contact member that contacts the skin and helps keep the skin taut during use. In some embodiments, the clipper attachment includes a comb structure that extends over the blade assembly and beyond blades of the blade assembly. The comb structure can be used to lift hair during a hair removal process.

Figure 1:
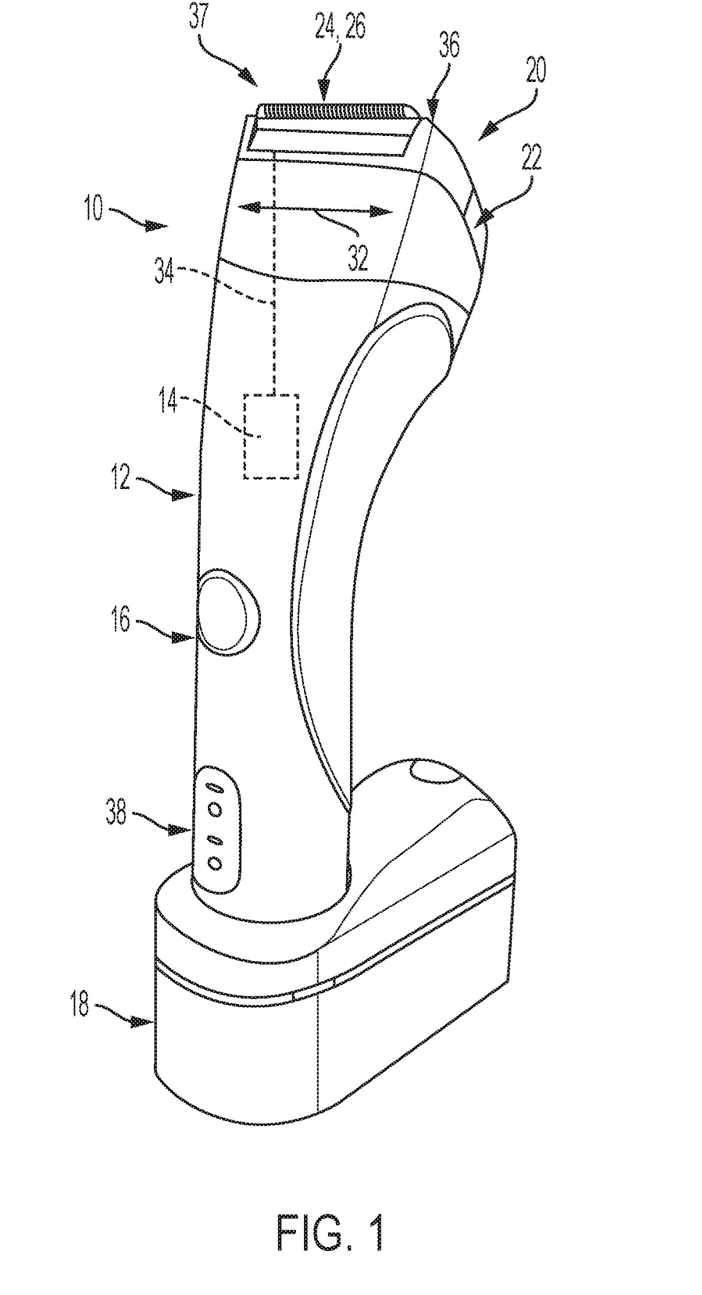
FIG. 1 illustrates a diagrammatic perspective view of a surgical hair clipper, according to one or more embodiments shown and described herein.

Referring to FIG. 1, a surgical hair clipper 10 includes a clipper body 12 that provides a housing for components of the surgical hair clipper, such as a motor (e.g., a rotary motor), which is illustrated schematically by element 14, and a user interface 16 that is used to control operation of the surgical hair clipper 10. The clipper body 12 may further include a rechargeable battery (e.g., a lithium battery) that can be recharged using a charging station 18.

A blade assembly 20 is connected to the clipper body 12. The blade assembly 20 includes a blade housing 22 and a moveable blade 26 that extends outwardly from the blade housing 22. In some embodiments, the blade assembly 20 may be removable from the clipper body 12 and be disposable. In other embodiments, the blade assembly 20 may be a permanent part of the clipper body 12 and may not be intended to be removable without damage to the surgical hair clipper 10. For removable blade assemblies 20, there may different blade assembly types, such as general purpose blade assembly for body hair, a neuro blade assembly for scalp and other thick, course hair and a sensitive blade assembly for perineal/sensitive areas. The blade assemblies may be intended for a single use.

Figure 2:
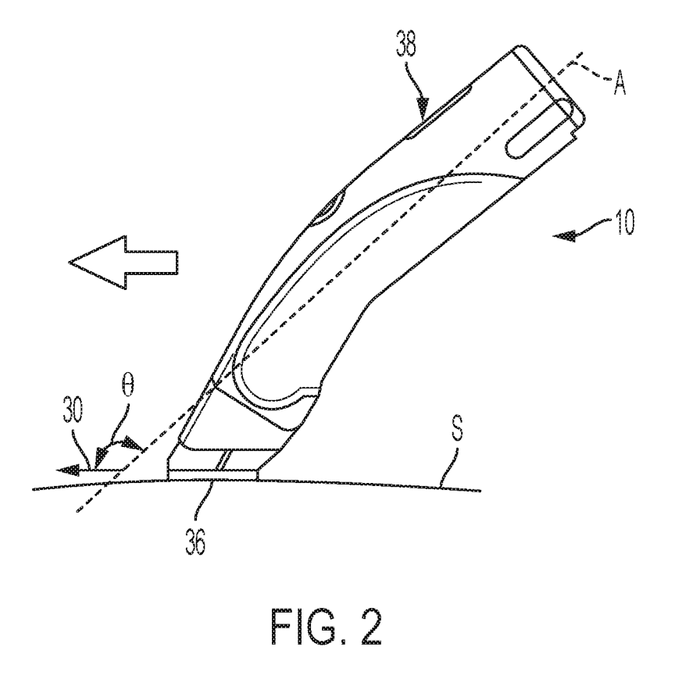
FIG. 2 illustrates a diagrammatic side view of the surgical hair clipper of FIG. 1 in use, according to one or more embodiments shown and described herein.

The blade assembly 20 includes the moveable blade 26 and a stationary blade 24 that both extend outwardly from a corner 28 of the blade housing 22 defining a blade cutting direction in the direction of arrow 30 (FIG. 2). The blades 24 and 26 have teeth that provide a comb-like shape across a width of the blades 24 and 26 defining a width direction in the direction of arrow 32 that is perpendicular to the blade cutting direction. The motor 14 reciprocates the moveable blade 26 in the width direction relative to the stationary blade 24 via a linkage 34 in order to cut hair located between the teeth.

The blade housing 22 includes a guide surface 36 that is located at a skin engagement end 37 of the surgical hair clipper 10. The guide surface 36 faces the skin S during a trimming operation. As can be seen, the guide surface 36 defines a plane that is substantially parallel with the cutting direction 30. In some embodiments, the cutting direction 30 and the guide surface 36 may be at an angle θ (e.g., between about 135 and about 145 degrees) that is oblique to a central axis A that passes through a base portion 38 of the blade housing 22 (FIG. 2).

Figure 3:
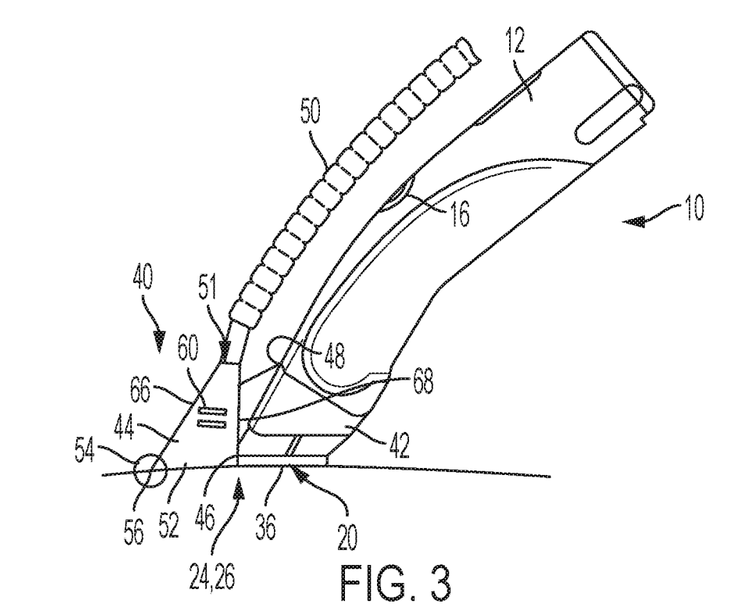
FIG. 3 is a diagrammatic side view of a surgical hair clipper assembly including a surgical hair clipper and a suction attachment, according to one or more embodiments shown and described herein.

As indicated above, referring to FIG. 3, a suction attachment 40 may be provided on the surgical hair clipper 10 providing a surgical hair clipper assembly. The suction attachment 40 includes a clipper attachment 42 and a nozzle structure 44 that is connected to the clipper attachment 42. In the illustrated example, the nozzle structure 44 and the clipper attachment 42 may be connected at multiple locations, such as at a distal location 46 and a proximal location 48. As used herein, the terms distal and proximal are with reference to an operator of the surgical hair clipper 10. For example, the blade assembly 20 is distal the user interface 16. The nozzle structure 44 may be, for example, molded with the clipper attachment 42 such that the suction attachment 40 is a single, monolithic part. In other embodiments, the nozzle structure 44 and the clipper attachment 42 may be formed separately and attached together, e.g., by welding, adhesive, etc.

The nozzle structure 44 may be connected to a hose 50 of a vacuum apparatus and may extend distally from the hose 50 at a hose connecting end 51 to a suction end 52 that is adjacent blades 24, 26 of the blade assembly 20. In some embodiments, the end 52 of the nozzle structure 44 may be located distal of the blades 24 and 26 such that the blades 24, 26 are located within the nozzle structure 44. In other embodiments, the end 52 may be located slightly proximal of or even with the blades 24, 26. The end 52 may include at least a portion that is nearly at or distal of the plane that is defined by the guide surface 36. For example, the end 52 may terminate at a single plane and be entirely located no more than ten millimeters proximal of the plane that is defined by the guide surface 36, such as no more than five mm, such as no more than two mm, such as no more than one mm.

In some embodiments, the end 52 of the nozzle structure 44 may be located so as to contact skin in front of the blades 24, 26 during a hair removal operation. To provide an engagement of the nozzle structure 44 with the skin area in front of the blades 24, 26, a leading side 66 of the nozzle structure 44 measured from the hose 50 may be longer than a trailing side 68 of the nozzle structure 44 in order to provide the end 52 that is substantially parallel to the plane that is defined by the guide surface 36.

To facilitate skin contact, the nozzle structure 44 may include a roller 54 that is located at the end 52. The roller 54 may be located at a leading edge 56 of the end 52. While a single roller 54 is illustrated, multiple rollers may be used. Further, the roller 54 may include a surface texture that helps to grip the skin and hold the skin taut. In some embodiments, the roller 54 may include a skin conditioning composition, such as, for example, low molecular weight water-soluble release enhancing agents (e.g., polyethylene glycol), water-swellable release enhancing agents (e.g., cross-linked polyacrylics), colorants, antioxidants, preservatives, vitamins, aloe, cooling agents, essential oils, astringents, lipids and/or medicinal agents. In some embodiments, the skin conditioning composition may be selected to augment a surgical prep procedure by utilizing compounds that work orthogonally to the active ingredients in many pre-surgical preps (e.g., alcohol, chlorhexidine gluconate (CHG), povidone-iodine (PVP-I) that can cause the hair to become sticky and more difficult to remove. The roller 54 may include a colorant in order to change color after use.

Figure 4:
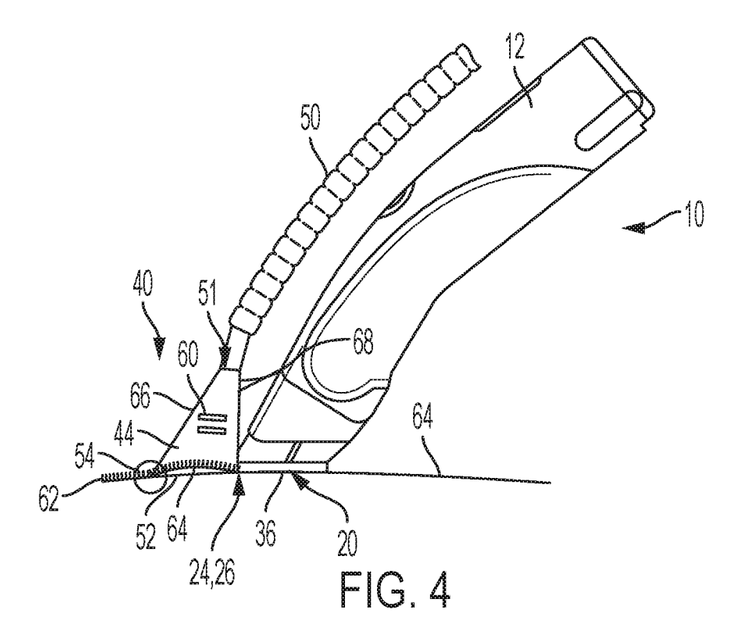
FIG. 4 is another diagrammatic side view of the surgical hair clipper assembly of FIG. 3 in use, according to one or more embodiments shown and described herein.

Referring also to FIG. 4, air vents 60 may be provided in the nozzle structure 44. The air vents 60 may be provided to limit the negative pressure within the nozzle structure during a hair removal procedure. While the negative pressure can be used to lift the hair 62 and skin 64 for cutting hair, the roller 54 and rest of the nozzle structure 44 including the roller 54 can inhibit excessive pulling of the skin 64 into the nozzle structure 44 while the air vents 60 also limit the negative pressure against the skin.

A method of using the surgical hair clipper 10 for hair removal from a skin surface of a patient may include coupling the blade assembly 20 to the clipper body 12. The blade assembly 20 includes, as described herein, the blades 24 and 26 and blade housing 22 having an aperture through which the blades 24 and 26 extend. The suction attachment 40 is connected to the surgical hair clipper 10 by inserting the blade assembly 20 into the clipper attachment 42.

Connecting the blade assembly 20 and clipper attachment 42 locates the nozzle structure 44 nearly at or distal of the plane that is defined by the guide surface 36. For example, the end 52 of the nozzle structure 44 may be located no more than ten millimeters proximal of the plane that is defined by the guide surface 36, such as no more than five mm, such as no more than two mm.

The method includes facing the guide surface 36 of the blade assembly 20 toward the skin area, and operating the blades 24, 26 through the clipper body 12 to remove hair from the skin area of the patient. As the blade assembly 20 is moved along the skin, the end 52 of the nozzle structure 44 may contact the skin and tauten the skin flat. In embodiments where a roller 54 is provided, the roller 54 may contact the skin and roll along the skin to facilitate movement of the nozzle structure 44 along the skin surface.

As described herein, the clipper body 12 of the surgical hair clipper 10 is configured to electronically operate the blades 24, 26. The clipper body 12 includes the enclosure housing an electrical motor and a battery, which battery is configured to be rechargeable through coupling of the clipper body 12 to the charging station 18 (FIG. 1). The clipper body 12 of the surgical hair clipper 10 further may include a charge indicator configured to indicate a low battery level of the battery below a predefined threshold. The method may include triggering an alarm through the charge indicator of the low battery level, coupling the body to the charging adaptor, and recharging the battery. The alarm may be a visual, audio, or tactile alarm. Such a visual alarm may be an LED light that may, for example, red to indicate the low battery level.

Figure 5:
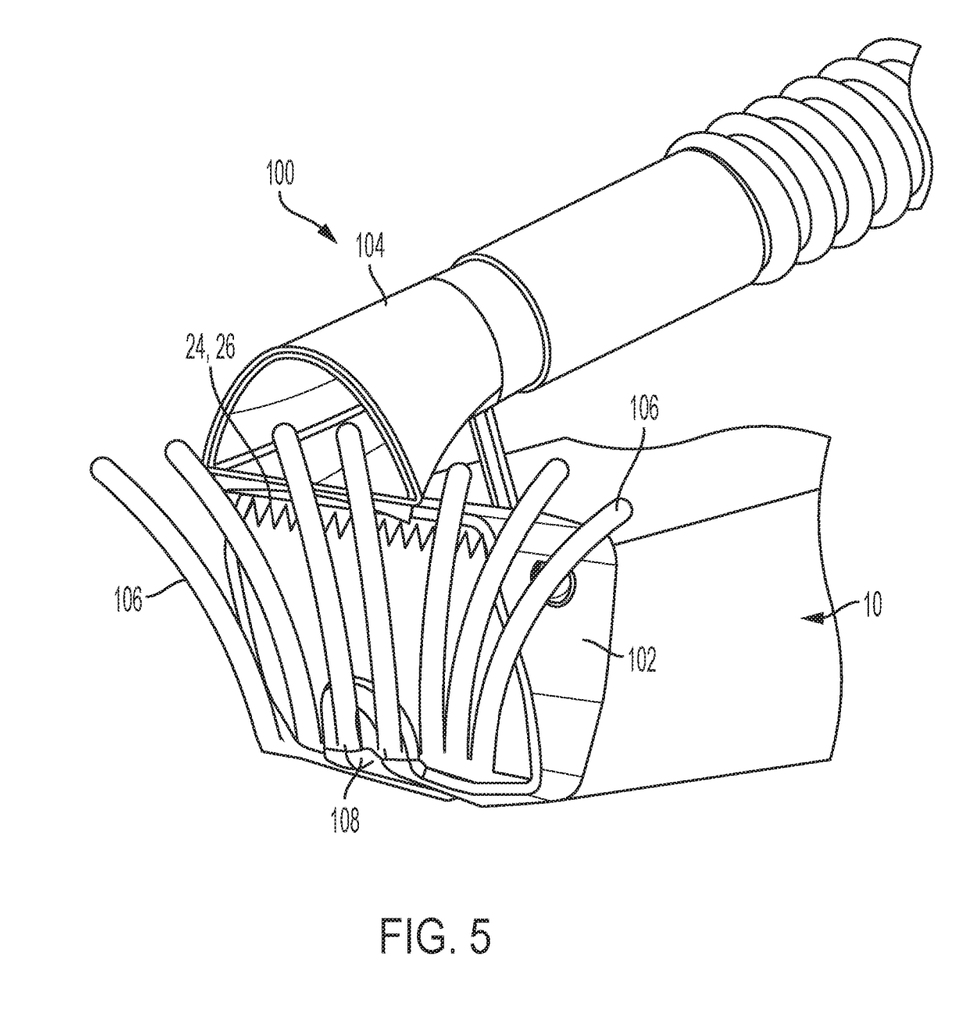
FIG. 5 is a diagrammatic perspective view of a surgical hair clipper assembly including a surgical hair clipper and a suction attachment, according to one or more embodiments shown and described herein.

Referring to FIG. 5, another embodiment of a suction attachment 100 includes a clipper attachment 102 and a nozzle structure 104 that is connected to the clipper attachment 102 in a fashion similar to that described above. In this embodiment, the clipper attachment 102 includes an array of hair conditioning projections 106 that extend generally in the cutting direction forming somewhat of a comb shape. In some embodiments, such as the one shown, two or more of the hair conditioning projections 106 may be flared or splayed relative to one another. In some embodiments, two or more of the hair conditioning projections 106 may be substantially parallel to one another.

The hair conditioning projections 106 may extend in the hair cutting direction from a trailing side 108 of the clipper attachment 102. The hair conditioning projections 106 may have lengths such that some or all of the hair conditioning projections 106 extend in the hair cutting direction beyond the cutting blades 24, 26 and underneath the nozzle structure 104. The hair conditioning projections 106 may be used to lift and separate hair as the hair clipper 10 is moved along the skin and may also apply tension to the skin to hold the skin taut.

Figure 6:
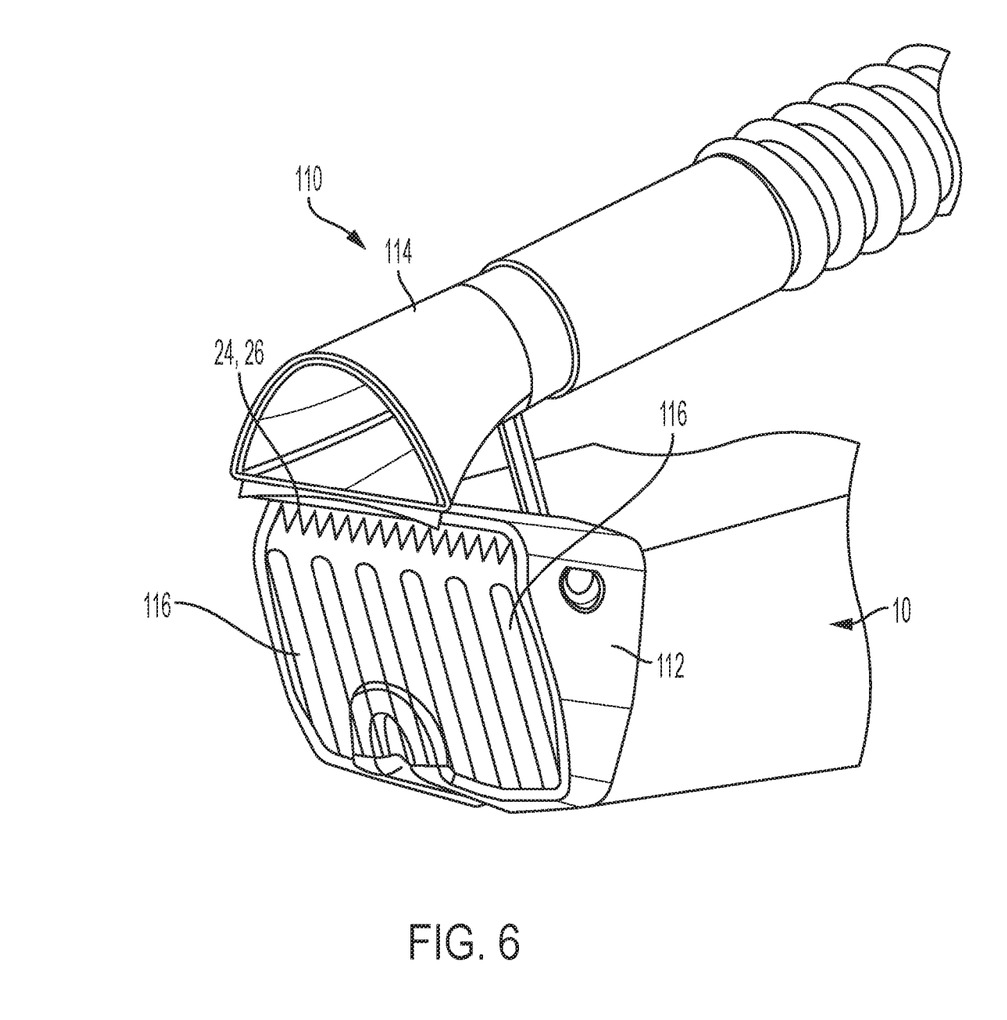
FIG. 6 is a diagrammatic perspective view of a surgical hair clipper assembly including a surgical hair clipper and a suction attachment, according to one or more embodiments shown and described herein.

FIG. 6 illustrates another embodiment of a suction attachment 110 that includes a clipper attachment 112 and a nozzle structure 114 that is connected to the clipper attachment 102. In this embodiment, an array of projections 116 extend generally parallel to the cutting direction forming a guard structure. The projections 116 may be used as the guard structure to set a clipping distance of the blades 24, 26 from the skin and may also apply tension to the skin to hold the skin taut. In the illustrated embodiment, the projections 116 terminate at a location behind the blades 24, 26 and do not extend beyond the blades 24, 26.

Figure 7:
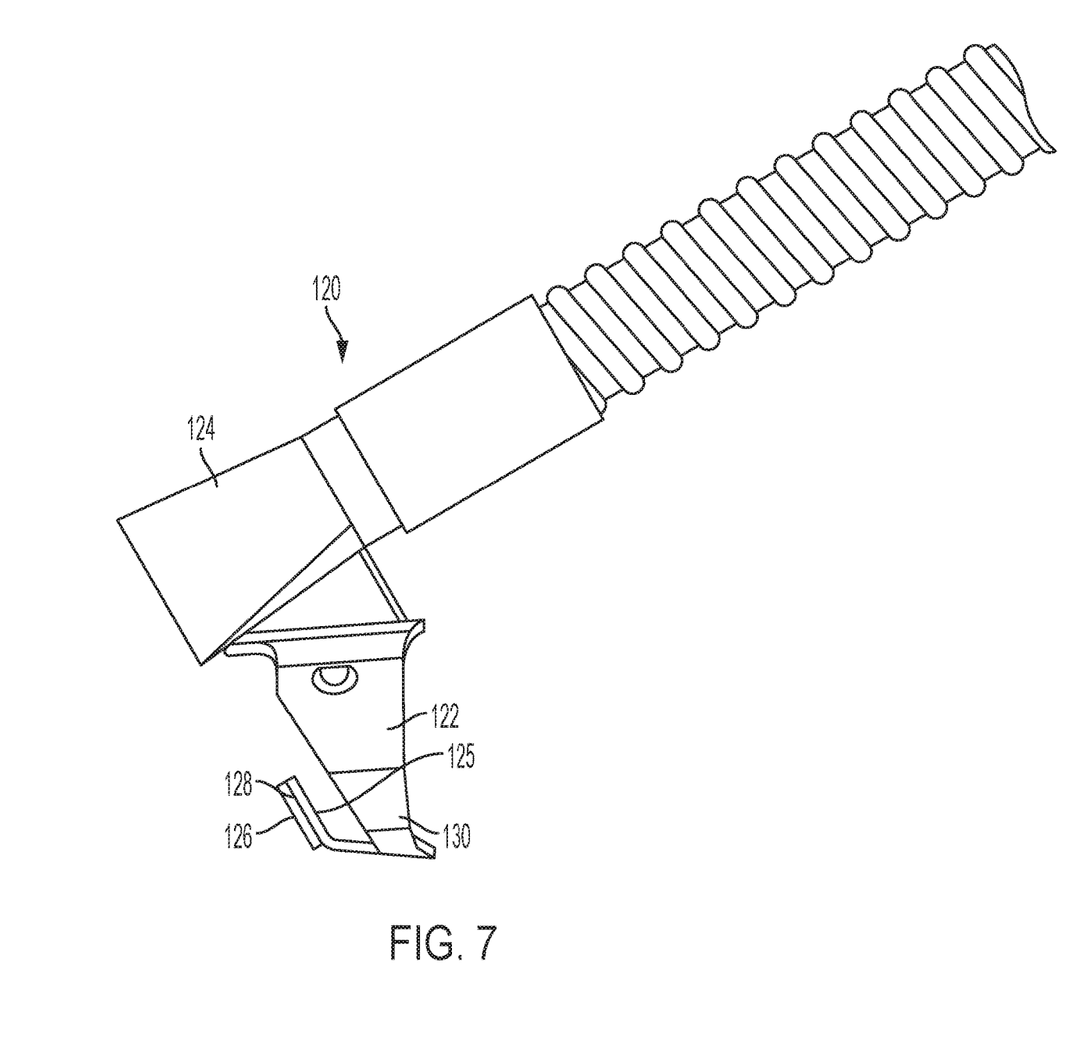
FIG. 7 is a side view of a suction attachment for use with a surgical hair clipper, according to one or more embodiments shown and described herein.

Referring to FIG. 7, another embodiment of a suction attachment 120 includes a clipper attachment 122 and a nozzle structure 124 that is connected to the clipper attachment 122. Projections 126 in the form of ribs may be provided on a skin facing surface 128 of an attachment member 125. The attachment member 125 may extend outwardly from an attachment body 130 of the clipper attachment 122. The attachment member 125 extends outward from the attachment body 130 along a height of the clipper body 12 and bends over a guide surface of the blade assembly 20 for positioning the attachment member 125 in place on the clipper body 12.

The above-described suction attachments can provide an elongated nozzle structure that extends alongside or even beyond the blades of the blade assembly to contact and tauten the skin during a hair clipping operation. Guides and/or ribs may be provided that encourage proper technique to enhance results and avoid nicking and toeing of skin. Use of comb structures can separate and prepare hair to be cut during the hair trimming operation, which can reduce the number of passes for satisfactory results.

The extended nozzle structure can cover an increased surface area to gather hair clippings thus resulting in quicker completion and more efficient hair removal. The suction attachments may include any number of projections that can provide a guard that can be used to control distance of the blades from the surface of the skin. The projections may include a skin conditioning composition located thereon, as discussed above.

Air vents may also be provided in the nozzle structure. The air vents may be openings in the nozzle structure that allow for passage of air into the nozzle structure to reduce negative pressure against the skin. In some embodiments, the air vents may be openings that are formed through the nozzle structure. In some embodiments, a structure may be provided that allows for opening and closing of the vents and can be controlled by an operator. In some embodiments, an air valve may be provided that controls entry of air based on a pressure within the nozzle structure.

Clause 1. A surgical hair clipper assembly comprising: a clipper body; a blade assembly connected to the clipper body, the blade assembly comprising a moveable blade configured to reciprocate to remove hair from a skin area and a blade housing that houses the moveable blade, the blade housing having a guide surface that faces the skin area during a hair removal process; and a suction attachment comprising: a clipper attachment connected to the clipper body; and a nozzle structure connected to the clipper attachment and extending distally to an end, the end being located no more than about ten millimeters proximal of a plane defined by the guide surface.

Clause 2. The surgical hair clipper assembly of clause 1, wherein a leading side of the nozzle structure is longer than a trailing side of the nozzle structure.

Clause 3. The surgical hair clipper assembly of clause 1 or 2, wherein the end is located no more than about two millimeters proximal of the plane defined by the guide surface.

Clause 4. The surgical hair clipper assembly of any one of clauses 1-3, wherein the end lies in a plane that is located distal of the moveable blade.

Clause 5. The surgical hair clipper assembly of any one of clauses 1-4, wherein the nozzle structure comprises a roller located at the end that contacts skin during use.

Clause 6. The surgical hair clipper assembly of any one of clauses 1-5, wherein the nozzle structure comprises air vents.

Clause 7. The surgical hair clipper assembly of any one of clauses 1-6, wherein the clipper attachment comprises a plurality of hair conditioning projections that extend in a hair cutting direction toward the moveable blade.

Clause 8. The surgical hair clipper assembly of clause 7, wherein the hair conditioning projections extend in the hair cutting direction beyond the moveable blade and over the nozzle structure.

Clause 9. A suction attachment comprising: a clipper attachment that connects to a clipper body of a surgical hair clipper; and a nozzle structure connected to the clipper attachment, the nozzle structure having a hose connecting end and a suction end; wherein a length of a leading side of the nozzle structure is greater than a length of a trailing side of the nozzle structure such that the suction end contacts a skin area during use.

Clause 10. The suction attachment of clause 9, wherein the nozzle structure comprises a roller located at the end that contacts the skin area during use.

Clause 11. The suction attachment of clause 9 or 10, wherein the nozzle structure comprises air vents.

Clause 12. The suction attachment of any one of clause 9-11, wherein the clipper attachment comprises a plurality of hair conditioning projections that extend in a hair cutting direction toward a moveable blade during use.

Clause 13. The suction attachment of clause 12, wherein the hair conditioning projections extend in the hair cutting direction beyond the moveable blade and over the nozzle structure during use.

Clause 14. The suction attachment of clause 13, wherein at least some of the hair conditioning projections are splayed relative to one another.

Clause 15. The suction attachment of any one of clauses 9-14, wherein the suction end is located proximal of a moveable blade of a surgical hair clipper during use.

Clause 16. A method of using a surgical hair clipper with a suction attachment, the method comprising: attaching a clipper attachment about a clipper body of the surgical hair clipper such that a nozzle structure of the suction attachment is located adjacent a blade assembly of the surgical hair clipper, the blade assembly comprises a blade housing having a guide surface that faces the skin area during a hair removal process, wherein the suction attachment comprises: the clipper attachment connected to the clipper body; the nozzle structure connected to the clipper attachment and extending distally to an end, the end being located no more than about ten millimeters proximal of a plane defined by the guide surface; and cutting hair while contacting a skin area of a patient with the end of the nozzle structure.

Clause 17. The method of clause 16, wherein a leading side of the nozzle structure is longer than a trailing side of the nozzle structure.

Clause 18. The method of clause 16 or 17, wherein the end is located no more than about two millimeters proximal of the plane defined by the guide surface.

Clause 19. The method of any one of clause 16-18, wherein the end lies in a plane that is located distal of the moveable blade.

Clause 20. The method of any one of clause 16-19, wherein the nozzle structure comprises a roller located at the end that contacts skin during use.

For the purposes of describing and defining the present disclosure, it is noted that recitations herein of "at least one" component, element, etc., should not be used to create an inference that the alternative use of the articles "a" or "an" should be limited to a single component, element, etc.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present disclosure it is noted that the terms "substantially" and "approximately" and "about" are utilized herein to represent the inherent degree of uncertainty that may be attributed to any quantitative comparison, value, measurement, or other representation. The terms "substantially" and "approximately" and "about" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A surgical hair clipper assembly comprising:
   a clipper body;
   a blade assembly connected to the clipper body, the blade assembly comprising a moveable blade configured to reciprocate to remove hair from a skin area and a blade housing that houses the moveable blade, the blade housing having a guide surface that faces the skin area during a hair removal process; and
   a suction attachment comprising:
     a clipper attachment connected to the clipper body;
     a plurality of hair conditioning projections that extend outward from the clipper attachment over the guide surface and toward the moveable blade; and
     a nozzle structure connected to the clipper attachment, the nozzle structure having a hose connecting end and a suction end defining a suction opening;
   wherein a trailing edge of the end of the nozzle structure is located in front of a leading edge of the moveable blade with the guide surface configured to be in contact with the skin area, the plurality of hair conditioning projections extending toward the trailing edge of the end of the nozzle structure.

2. The surgical hair clipper assembly of claim 1, wherein a leading side of the nozzle structure is longer than a trailing side of the nozzle structure.

3. The surgical hair clipper assembly of claim 1, wherein the end is located no more than two millimeters proximal of the guide surface.

4. The surgical hair clipper assembly of claim 1, wherein the end lies in a plane that is located distal of the moveable blade.

5. The surgical hair clipper assembly of claim 1, wherein the nozzle structure comprises a roller located at the end that contacts skin during use.

6. The surgical hair clipper assembly of claim 1, wherein the nozzle structure comprises air vents.

7. The surgical hair clipper assembly of claim 1, wherein the end being located no more than ten millimeters proximal of the guide surface.

8. The surgical hair clipper assembly of claim 1, wherein the hair conditioning projections extend beyond the moveable blade and over the nozzle structure.

9. A suction attachment and surgical hair clipper system, comprising:
   a clipper attachment that connects to a clipper body of the surgical hair clipper;
   a plurality of hair conditioning projections that extend outward from the clipper attachment and configured to extend over a guide surface of a blade housing of the surgical hair clipper and toward a moveable blade of a blade assembly; and
   a nozzle structure connected to the clipper attachment, the nozzle structure having a hose connecting end and a suction end defining a suction opening;
   wherein a trailing edge of the suction end is configured to be located in front of a leading edge of the moveable blade, the plurality of hair conditioning projections configured to extend toward the trailing edge of the suction end.

10. The suction attachment and surgical hair clipper system of claim 9, wherein the nozzle structure comprises a roller located at the end that contacts the skin area during use.

11. The suction attachment and surgical hair clipper system of claim 9, wherein the nozzle structure comprises air vents.

12. The suction attachment and surgical hair clipper system of claim 9, wherein the hair conditioning projections extend beyond the moveable blade and over the nozzle structure during use.

13. The suction attachment and surgical hair clipper system of claim 12, wherein at least some of the hair conditioning projections are splayed relative to one another.

14. The suction attachment and surgical hair clipper system of claim 9, wherein the suction end is located proximal of a moveable blade of a surgical hair clipper during use.

* * * * *

UNITED STATES PATENT AND TRADEMARK OFFICE
CERTIFICATE OF CORRECTION

PATENT NO. : 12,330,323 B2
APPLICATION NO. : 17/072515
DATED : June 17, 2025
INVENTOR(S) : Isaias Tellez et al.

It is certified that error appears in the above-identified patent and that said Letters Patent is hereby corrected as shown below:

In the Claims

In Column 8, Line(s) 59, Claim 1, delete "end" and insert --suction end--, therefor.

In Column 9, Line(s) 2, Claim 3, delete "end" and insert --suction end--, therefor.

In Column 9, Line(s) 5, Claim 4, delete "end" and insert --suction end--, therefor.

In Column 9, Line(s) 8, Claim 5, delete "end" and insert --suction end--, therefor.

In Column 9, Line(s) 13, Claim 7, delete "end" and insert --suction end--, therefor.

In Column 9, Line(s) 13, Claim 7, delete "being" and insert --is--, therefor.

In Column 10, Line(s) 11, Claim 10, delete "end" and insert --suction end--, therefor.

Signed and Sealed this
Nineteenth Day of August, 2025

Coke Morgan Stewart
*Acting Director of the United States Patent and Trademark Office*